US012627043B2

(12) United States Patent
Laubenthal

(10) Patent No.: US 12,627,043 B2
(45) Date of Patent: May 12, 2026

(54) REAL TIME BUR CHATTER COMPENSATION IN SURGICAL CUTTING BURS

(71) Applicant: Stryker Corporation, Kalamazoo, MI (US)

(72) Inventor: Michael Laubenthal, Mattawan, MI (US)

(73) Assignee: Stryker Corporation, Portage, MI (US)

( * ) Notice: Subject to any disclaimer, the term of this patent is extended or adjusted under 35 U.S.C. 154(b) by 241 days.

(21) Appl. No.: 18/279,616

(22) PCT Filed: Mar. 1, 2022

(86) PCT No.: PCT/US2022/018325
§ 371 (c)(1),
(2) Date: Sep. 1, 2023

(87) PCT Pub. No.: WO2022/187234
PCT Pub. Date: Sep. 9, 2022

(65) Prior Publication Data
US 2024/0138852 A1 May 2, 2024

Related U.S. Application Data

(60) Provisional application No. 63/155,142, filed on Mar. 1, 2021.

(51) Int. Cl.
*H02M 3/24* (2006.01)
*A61B 17/16* (2006.01)
(Continued)

(52) U.S. Cl.
CPC ....... *H01Q 3/2694* (2013.01); *A61B 17/1615* (2013.01); *H01Q 3/28* (2013.01);
(Continued)

(58) Field of Classification Search
CPC ...... H01Q 3/2694; H01Q 3/28; H01Q 13/103; H01Q 15/0086; A61B 17/1615
See application file for complete search history.

(56) References Cited

U.S. PATENT DOCUMENTS

| | | | |
|---|---|---|---|
| 4,116,200 A | 9/1978 | Braun et al. | |
| 5,076,807 A | 12/1991 | Bezwada et al. | |

(Continued)

FOREIGN PATENT DOCUMENTS

| | | | |
|---|---|---|---|
| CA | 2037422 A1 | 2/1992 | |
| CA | 2115108 A1 | 8/1994 | |

(Continued)

OTHER PUBLICATIONS

International Search Report for Application No. PCT/US2022/018325 dated May 9, 2022, 2 pages.

(Continued)

*Primary Examiner* — Muhammad S Islam
(74) *Attorney, Agent, or Firm* — Howard & Howard Attorneys PLLC

(57) ABSTRACT

A surgical console system configured to provide a drive signal to a surgical instrument for rotating a surgical bur. The surgical console system may supply a first drive signal to the surgical instrument to rotate the bur at a desired speed and to determine an electrical current drawn by the surgical instrument based on the drive signal. The surgical console system may be further configured to identify a chatter event based on the electrical current, and to supply a second drive signal to the surgical instrument based on the identified chatter event.

20 Claims, 4 Drawing Sheets

(51) Int. Cl.

| | | |
|---|---|---|
| *H01Q 3/26* | (2006.01) |
| *H01Q 3/28* | (2006.01) |
| *H04B 1/40* | (2015.01) |
| *A61B 17/00* | (2006.01) |

(52) U.S. Cl.

CPC ...... *H04B 1/40* (2013.01); *A61B 2017/00199* (2013.01); *A61B 2017/00973* (2013.01)

(56) References Cited

U.S. PATENT DOCUMENTS

| | | | |
|---|---|---|---|
| 5,104,411 | A | 4/1992 | Makoui et al. |
| 5,170,358 | A | 12/1992 | Delio |
| 5,294,770 | A | 3/1994 | Riddle et al. |
| 5,374,260 | A | 12/1994 | Lemay et al. |
| 5,477,604 | A | 12/1995 | Smith et al. |
| 5,494,359 | A | 2/1996 | Del Rio et al. |
| 5,538,423 | A | 7/1996 | Coss et al. |
| 5,713,876 | A | 2/1998 | Bogert et al. |
| 5,784,273 | A | 7/1998 | Madhavan |
| 5,916,582 | A | 6/1999 | Stevenson et al. |
| 5,932,547 | A | 8/1999 | Stevenson et al. |
| 5,968,365 | A | 10/1999 | Laurenzo et al. |
| 6,017,354 | A | 1/2000 | Culp et al. |
| 6,085,121 | A | 7/2000 | Stern |
| 6,183,499 | B1 | 2/2001 | Fischer et al. |
| 6,616,446 | B1 | 9/2003 | Schmid |
| 7,536,237 | B2 | 5/2009 | Esterling |
| 9,138,848 | B2 | 9/2015 | Ueno |
| 9,179,923 | B2 | 11/2015 | Gubellini et al. |
| 9,186,156 | B2 | 11/2015 | Xie |
| 9,381,608 | B2 | 7/2016 | Tanaka |
| 9,808,246 | B2 | 11/2017 | Shelton, IV et al. |
| 10,042,922 | B2 | 8/2018 | Besuchet et al. |
| 10,226,276 | B2 | 3/2019 | Kessler |
| 10,238,386 | B2 | 3/2019 | Overmyer et al. |
| 10,321,920 | B2 | 6/2019 | McGinley |
| 10,448,948 | B2 | 10/2019 | Shelton, IV et al. |
| 11,426,193 | B2 | 8/2022 | Kessler |
| 2001/0034528 | A1 | 10/2001 | Foerster et al. |
| 2003/0040291 | A1 | 2/2003 | Brewer |
| 2003/0083713 | A1 | 5/2003 | Palreddy et al. |
| 2003/0116260 | A1 | 6/2003 | Chobotov et al. |
| 2004/0138738 | A1 | 7/2004 | Stinson |
| 2004/0193227 | A1 | 9/2004 | Schmidt |
| 2005/0116673 | A1 | 6/2005 | Carl |
| 2005/0177168 | A1 | 8/2005 | Brunnett et al. |
| 2006/0036235 | A1 | 2/2006 | Swoyer et al. |
| 2006/0145871 | A1 | 7/2006 | Donati et al. |
| 2007/0244486 | A1 | 10/2007 | Hogg et al. |
| 2008/0109042 | A1 | 5/2008 | Bodner et al. |
| 2008/0228137 | A1 | 9/2008 | Aljuri et al. |
| 2009/0073991 | A1 | 3/2009 | Landrum et al. |
| 2009/0234410 | A1 | 9/2009 | Libbus et al. |
| 2009/0264792 | A1 | 10/2009 | Mazar |
| 2009/0292194 | A1 | 11/2009 | Libbus et al. |
| 2010/0037901 | A1 | 2/2010 | Rousseau et al. |
| 2010/0056881 | A1 | 3/2010 | Libbus et al. |
| 2010/0204745 | A1 | 8/2010 | Li et al. |
| 2010/0211184 | A1 | 8/2010 | Rousseau et al. |
| 2010/0217267 | A1 | 8/2010 | Bergin et al. |
| 2010/0234716 | A1 | 9/2010 | Engel |
| 2010/0298833 | A1 | 11/2010 | Smith |
| 2011/0015660 | A1* | 1/2011 | Wiener .............. A61B 18/1445 606/169 |
| 2011/0245711 | A1 | 10/2011 | Katra et al. |
| 2011/0270049 | A1 | 11/2011 | Katra et al. |
| 2012/0108917 | A1 | 5/2012 | Libbus et al. |
| 2012/0179161 | A1 | 7/2012 | Rains et al. |
| 2012/0259338 | A1 | 10/2012 | Carr et al. |
| 2013/0138004 | A1 | 5/2013 | Dong et al. |
| 2013/0274750 | A1 | 10/2013 | Schoutens |
| 2013/0274779 | A1 | 10/2013 | Kulas et al. |
| 2013/0310866 | A1* | 11/2013 | Belagali ............. A61B 17/1615 606/180 |
| 2014/0107399 | A1 | 4/2014 | Spence |
| 2014/0123740 | A1 | 5/2014 | Yoshikawa et al. |
| 2015/0025559 | A1 | 1/2015 | Kulas et al. |
| 2015/0126822 | A1 | 5/2015 | Chavan et al. |
| 2016/0030752 | A1 | 2/2016 | Mahajan et al. |
| 2016/0287250 | A1 | 10/2016 | Shelton, IV et al. |
| 2016/0287253 | A1 | 10/2016 | Shelton, IV et al. |
| 2017/0056026 | A1 | 3/2017 | Vu et al. |
| 2017/0120451 | A1 | 5/2017 | Hauser et al. |
| 2017/0348064 | A1* | 12/2017 | Stewart .............. A61B 18/1445 |
| 2018/0014846 | A1* | 1/2018 | Rhee .............. A61B 17/320092 |
| 2018/0157238 | A1 | 6/2018 | Gogarty et al. |
| 2018/0368839 | A1 | 12/2018 | Shelton, IV et al. |
| 2018/0368840 | A1 | 12/2018 | Shelton, IV et al. |
| 2018/0368841 | A1 | 12/2018 | Shelton, IV et al. |
| 2019/0159802 | A1 | 5/2019 | Kessler |
| 2019/0201027 | A1 | 7/2019 | Shelton, IV et al. |
| 2019/0201041 | A1* | 7/2019 | Kimball ................. A61B 34/30 |
| 2019/0380788 | A1 | 12/2019 | Becker et al. |
| 2022/0338938 | A1* | 10/2022 | Walen ................ A61B 17/1628 |

FOREIGN PATENT DOCUMENTS

| | | | |
|---|---|---|---|
| DE | 2520946 | A1 | 11/1976 |
| EP | 0759305 | A2 | 2/1997 |
| GB | 1379660 | A | 1/1975 |
| KR | 101587721 | B1 | 1/2016 |
| WO | 9800152 | A1 | 1/1998 |
| WO | 2018033490 | A1 | 2/2018 |
| WO | 2019232375 | A2 | 12/2019 |
| ZA | 975942 | B | 4/1998 |

OTHER PUBLICATIONS

English language abstract and machine-assisted English translation for DE 25 20 946 A1 extracted from espacenet.com database on Sep. 4, 2023, 9 pages.

English language abstract for KR 101587721 B1 extracted from espacenet.com datatbase on Sep. 4, 2023, 1 page and machine-assisted English translation for KR 101587721B1 extracted from Korean Patent Office on Jun. 7, 2022, 43 pages.

English language abstract and machine-assisted English translation for WO 2018/033490 A1 extracted from espacenet.com database on Sep. 4, 2023, 17 pages.

English language abstract for ZA 975942 B extracted from espacenet. com database on Sep. 4, 2023, 2 pages.

\* cited by examiner

REAL TIME BUR CHATTER COMPENSATION IN SURGICAL CUTTING BURS

CROSS-REFERENCE TO RELATED APPLICATIONS

The subject patent application is the National Stage of International Patent Application No PCT/US2022/018325, filed on Mar. 1, 2022, which claims priority to, and all the benefits of, U.S. Provisional Patent Application No. 63/155, 142, filed on Mar. 1, 2021, the entire contents of which are incorporated by reference herein.

BACKGROUND

Surgical burs often operate at speeds upwards of 5,000 RPM. At such speeds, vibration must be minimized at the contact between tissue and surgical bur. The bur itself is often designed to minimize this vibration, however, there is also a need for other aspects of the surgical bur system to further counter this vibration. It is the object of this disclosure to discuss methods by which the vibration may be countered in real time by the surgical bur system.

SUMMARY

In one aspect, a surgical console system configured to provide a drive signal to a surgical instrument comprising a rotatable bur. The surgical console system may comprise a processor and a memory. The memory may store instructions executable by the processor to supply a first drive signal to the surgical instrument to rotate the bur at a desired speed and to determine an electrical current drawn by the surgical instrument based on the drive signal. The memory may further store instructions to identify a chatter event based on the electrical current, and to supply a second drive signal to the surgical instrument based on the identified chatter event. In one implementation of this aspect, the second drive signal supplied to the surgical instrument may rotate the bur at an alternate speed. In another implementation of this aspect, the instruction to identify a chatter event is further defined as analyzing the electrical current to generate a harmonic signature.

In another aspect, a surgical bur system capable of rotating a surgical bur at a speed of at least 5,000 RPM. The surgical bur system may comprise a handheld surgical instrument and a console in communication with the handheld surgical instrument. The handheld surgical instrument may comprise a body, a motor disposed in the body, and a surgical bur coupled to the motor and configured to rotate relative to the body. The console may be configured to provide a first drive signal to the motor. The console may comprise a processor and a memory. The memory may store instructions executable by the processor to supply a drive signal to the handheld surgical instrument to rotate the surgical bur at a desired speed and to determine an electrical current drawn by the handheld surgical instrument based on the drive signal. The memory may further store instructions to identify a chatter event based on the electrical current, and to supply a second drive signal to the handheld surgical instrument based on the identified chatter event. In one implementation of this aspect, the second drive signal supplied to the surgical instrument may rotate the bur at an alternate speed. In another implementation of this aspect, the instruction to identify a chatter event is further defined as analyzing the electrical current to generate a harmonic signature.

Any of the above aspects can be combined in full or in part. Any features of the above aspects can be combined in full or in part. Any of the above implementations for any aspect can be combined with any other aspect. Any of the above implementations can be combined with any other implementation whether for the same aspect or a different aspect.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
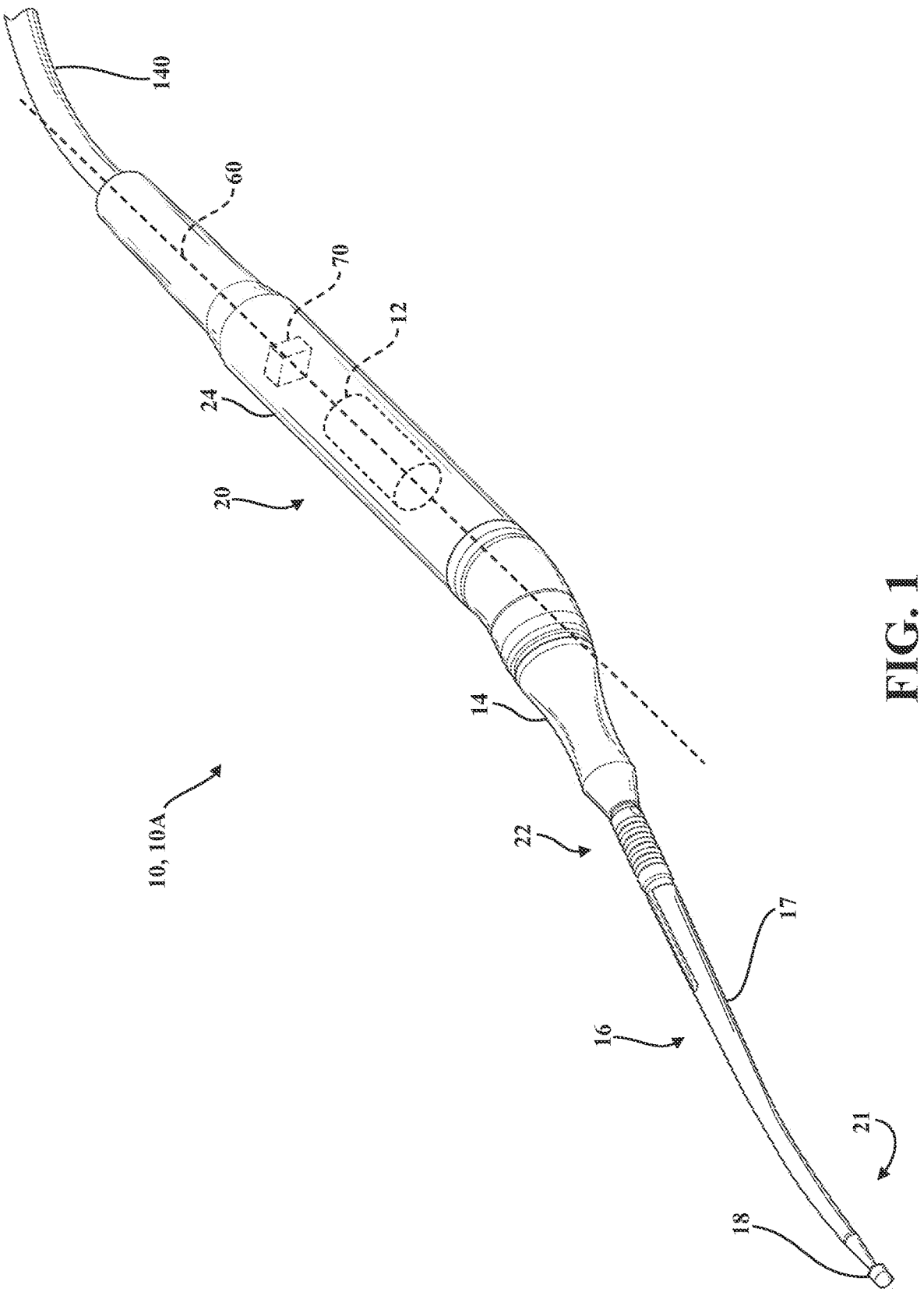
FIG. 1 is a perspective view of a handheld surgical instrument including a hub coupled to a nose tube assembly.

Referring now to the drawings, a surgical console system 132 and a surgical bur system 120 having an operational control system for a surgical instrument 10 are disclosed. In particular, embodiments of the operational control mechanism may be suitable for use with a broad selection of instruments such as surgical drills, saws, and like devices.

As one example, the surgical instrument 10 may comprise a specialty drill such as one sold under the brand name CORE UNIVERSAL SERIES by Stryker Instruments of Kalamazoo, Michigan, United States. Other examples of the surgical instrument 10 may comprise: a high-powered tapered drill, such as one sold under the brand name CORE SUMEX DRILL by Stryker Instruments; a modular handpiece such as one sold under the brand name CORE UNIVERSAL DRIVER by Stryker Instruments; a high-speed pencil-grip drill such as one sold under the brand name CORE MICRO DRILL by Stryker; a pneumatic drill such as one sold under the brand name MAESTRO DRILL by Stryker; a drill for intraoperative procedures such as one sold under the brand name ARIA MRI DRILL SYSTEM by Stryker; a drill for oral surgery such as one sold under the brand name CORE IMPACTION DRILL by Stryker; a drill for ENT surgery sold under the brand name SABER DRILL by Stryker; a microdebrider such as one sold under the brand name ESSX MICRODEBRIDER. Other handheld surgical instruments sold by Stryker or any manufacturer are also contemplated.

Further, it is understood that this disclosure is not specific to a type of surgical bur used with the instrument 10. Examples of the surgical bur may comprise various burs for small bone procedures such as those sold under the brand names M TOOL BUR, AM TOOL BUR, ELITE BUR, ZYPHR BUR, MIS BUR, and TPS BUR by Stryker. Other surgical burs sold by Stryker or any manufacturer are also contemplated.

Referring now to FIG. 1, one non-limiting example of a suitable handheld surgical instrument, for use with a controller 70 described below, is generally indicated at 10. It is understood that the controller 70 may be used with other types of surgical instruments and is not necessarily limited to high-speed surgical drills, such as those that rotate, for example, 5,000 revolutions per minute (5k RPM). High speed surgical drills, as a non-limiting example, operate at speeds of at least 5k, 10k, 15k,'k, 25k, or 30k RPM and the speeds could be up to 50k, 60k, 70k, 80k, 90k, or 100k RPM.

FIG. 1 depicts a perspective view of a handheld surgical instrument 10, illustrated as a high-speed drill 10A. The handheld surgical instrument 10 may comprise a handpiece body 24, a motor 12 disposed in the handpiece body 24, a hub 14, and a nose tube assembly 16. The hub 14 is coupled to the handpiece body 24 and engaged with the motor 12 in a torque translating relationship. The hub 14 is further coupled to the nose tube assembly 16. The nose tube assembly 16 includes a nose tube 17, a driveshaft (not pictured) operatively coupled to the motor 12, and a surgical bur 18 coupled to the driveshaft. The motor 12 is configured to provide torque through the hub 14 to the nose tube assembly 16. Specifically, the motor 12 transfers torque through the hub 14 to the driveshaft of the nose tube assembly 16, which rotates the surgical bur 18 disposed at a distal end 21 of the nose tube assembly 16. The motor 12 is configured to transfer torque through the hub 14 and the nose tube assembly 16 to the surgical bur 18. In some configurations, the motor 12 may be configured to rotate the surgical bur 18 at speeds greater than 50k RPM. The high-speed torque transfer from the motor 12 to the surgical bur 18 allows the surgical bur 18 to accurately and efficiently remove tissue, for example from a patient's nasal passage. The nose tube assembly 16 may also be adapted for spinal, neuro, and endoscopic applications. The above exemplary driveshaft is described in greater detail in U.S. Patent No. 9,186,156 issued on Nov. 17, 2015, which is incorporated by reference herein in its entirety. The handheld surgical instrument could alternatively be a shaver or twist drill.

The hub 14 may include a variety of different configurations. The hub 14 may be straight, angled, or curved depending on use and/or preference of the operator. For example, in a curved configuration, the hub 14 may define a twenty-degree seamless curve away from a horizontal axis 60 of the hub 14, or the hub 14 may define a straight length along the horizontal axis 60. Additionally, the nose tube assembly 16 may also be curved or straight depending on application of the nose tube assembly 16. More specifically, the nose tube 17 may be curved or straight. For example, the nose tube assembly 16 may include a bend at a proximal end 22, or may include a bend at the distal end 21 of the nose tube assembly 16. Transnasal applications of the nose tube assembly 16 may employ a bend at the distal end 21, and spinal applications of the nose tube assembly 16 may employ a bend at the proximal end 22 of the nose tube assembly 16. Bushings (not shown) align the driveshaft within a lumen of the nose tube 17 so that the driveshaft does not contact an inner surface of the nose tube 17. This allows the driveshaft to rotate independently of the nose tube 17 when the motor 12 transfers torque through the driveshaft.

As stated above, the hub 14 attaches to the motor 12. The hub 14 may include features that aid in aligning and locking the hub 14 to the motor 12 of the surgical instrument 10. For example, the hub 14 may include a visual indicator such as a dot (not shown) that corresponds to another dot (not shown) on the motor 12 such that alignment between the dots allows the hub 14 to couple to the motor 12. Additionally, the hub 14 may include an anti-rotation pin (not shown) at the proximal end 22 of the hub 14 to allow specific orientations between the hub 14 and the motor 12. An external c-clip (not shown) as well as an O-ring (not shown) may further aid to establish a secure connection between the hub 14 and the motor 12 such that the motor 12 transfers torque through the hub 14 to the nose tube assembly 16. The hub 14 may also include a knurled portion (not shown). The knurled portion corresponds to a position on the hub 14 where an operator may place a finger to hold the surgical instrument 10.

During operation of the surgical instrument 10, the rotating surgical bur 18 contacts a tissue surface to remove material. Material removal by the rotating surgical bur 18 may induce vibration in the surgical bur 18 at a frequency that may be proportional to the rotational speed of the surgical bur 18 and, in some cases, one or more parameters of the surgical bur 18, such as the quantity of cutting surfaces (flutes) on the surgical bur 18. As the handheld surgical instrument 10 is operated, the vibration frequency of the surgical bur 18 may resonate against the tissue surface, which may result in "chatter". Bur chatter may be described as back and forth vibrations of a bur head against the tissue surface that is being cut. Chatter may be reduced by modifying operational parameters of the handheld surgical instrument 10 to prevent resonance of the surgical bur 18. For example, changing parameters such as the rotational speed of the surgical bur 18, the natural frequency of the surgical bur 18, and the pressure of the surgical bur 18 on the tissue surface may reduce, lessen, or otherwise eliminate chatter. The natural frequency of the surgical bur 18 cannot be easily modified in situ during operation, and the pressure of the surgical bur 18 on the tissue surface, while controllable by the user, may have a very small range of acceptability due to the nature of the tissue. A system and method for detecting and reducing chatter through control of the rotational speed of the surgical bur 18 is explained in further detail below.

Resonance from chatter may cause the surgical bur 18 to flex in a periodic manner. As the surgical bur 18 flexes, the contact pressure between the surgical bur 18 and the tissue may fluctuate in a similarly periodic nature. This fluctuation of pressure may result in the flutes of the surgical bur 18 removing tissue non-uniformly and in a periodic nature. Said differently, each flute may remove a different amount of tissue than a preceding or following flute. Because the amount of tissue removed by each flute is fluctuating, the power required by each flute to cut the tissue fluctuates in a corresponding relationship and, as such, the torque required to rotate the surgical bur 18 fluctuates. As the torque on the surgical bur 18 changes, the power required by the motor 12 fluctuates in the same way, which is related to electrical current drawn by the motor 12. The controller 70 can measure or otherwise determine the electrical current drawn by the motor 12 of the handheld surgical instrument 10, among other electrical characteristics, with respect to time in order to approximate an instantaneous, or near-instantaneous, torque produced by the motor 12. As used herein, electrical current, or current, generally refers to the flow of electric charge and may be measured in amperes or "amps".

The controller 70 is configured to measure an electrical current drawn by the handheld surgical instrument 10 during operation. The measured electrical current is related to the operational state of the handheld surgical instrument 10 and characteristics at a point of contact between the tissue and the surgical bur 18. After sensing the current drawn by the handheld surgical instrument 10, the controller 70 is further configured to identify a chatter event based on the measured electrical current or other electrical parameter, such as voltage or power. The chatter event may be a result of undesirable vibration occurring at the tissue-bur contact or other non-uniformity in the tissue removal process, such as a localized area of harder tissue. If controller 70 identifies a chatter event, or determines that a chatter event exists, the controller 70 may supply a second drive signal to the surgical instrument 10 based on the identified chatter event, the second drive signal differing from the first drive signal in at least one characteristic. For example, the controller 70 may analyze the electrical current to detect and identify a chatter event and, based on the identified chatter event, adjust the rotational speed of the surgical bur 18. Subsequently, the controller 70 may perform further analysis on the electrical current drawn by the motor 12 to determine whether the chatter event is still present or a new chatter event is detected after the adjustment, and resume normal operation once the chatter event is no longer detected.

Figures 2A, 2B, 2D:
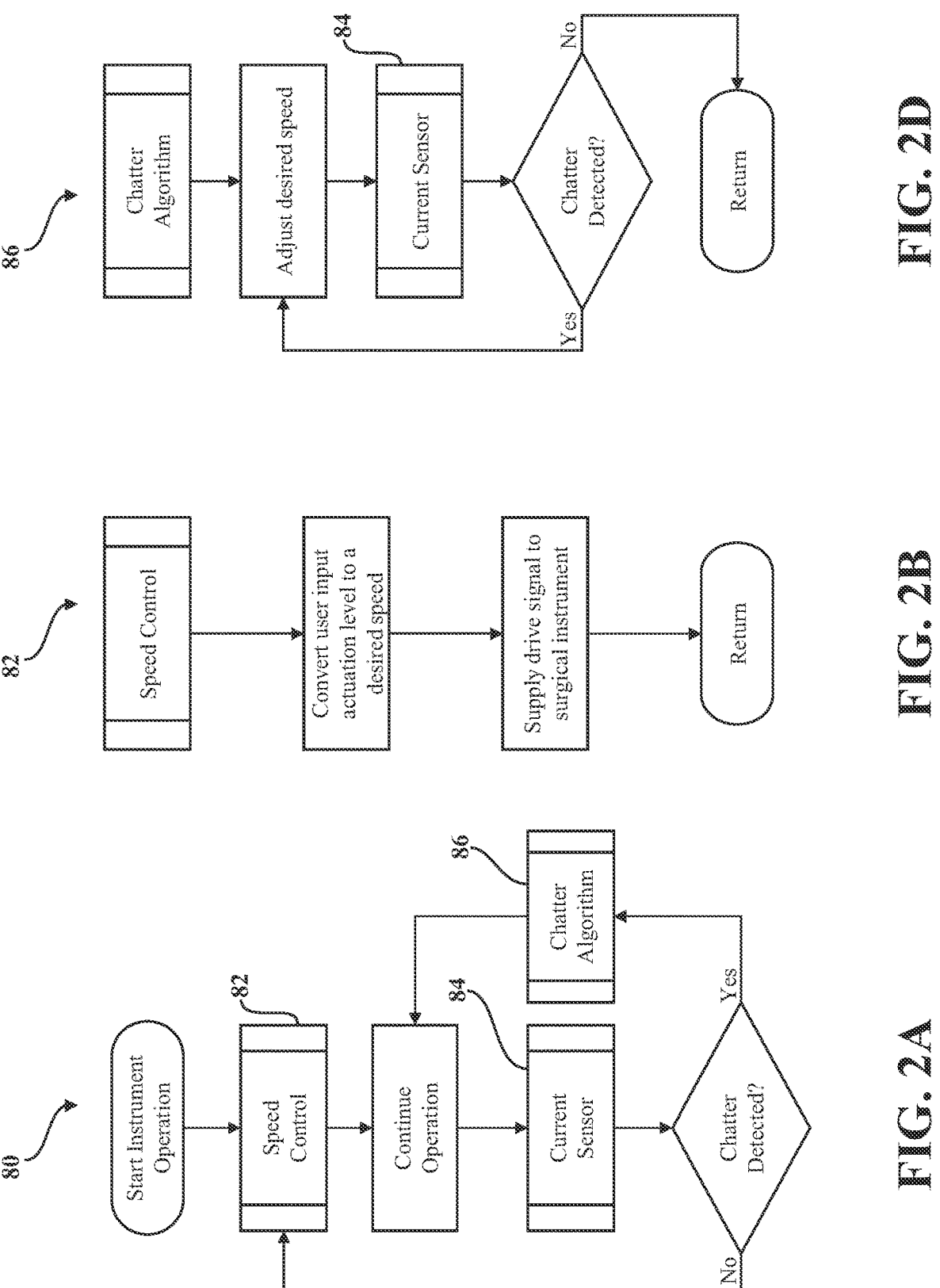
FIG. 2A is a flow diagram representing an operating process of the handheld surgical instrument.
FIG. 2B is a flow diagram representing a speed control process for the handheld surgical instrument.
FIG. 2D is a flow diagram representing a chatter algorithm process for the handheld surgical instrument.
Figure 2C:
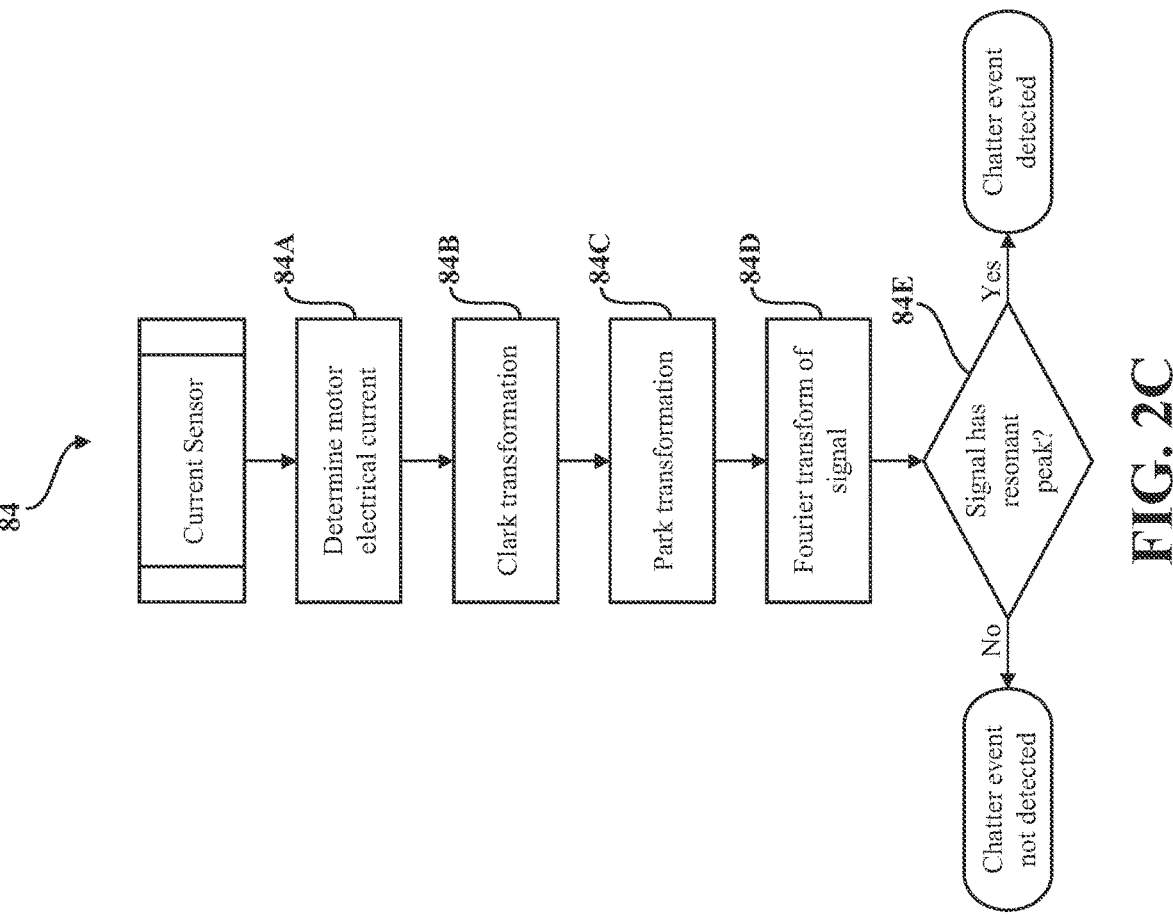
FIG. 2C is a flow diagram representing a current sensor process for the handheld surgical instrument.

Referring now to the schematic diagrams in FIGS. 2A-D, FIG. 2A depicts an exemplary operation process 80 of the handheld surgical instrument 10, FIG. 2B depicts a speed control process 82, FIG. 2C depicts a current sensor process 84, and FIG. 2D depicts a chatter algorithm process 86 at a high level. The operation process shown in FIG. 2A starts with a call to the speed control process 82 shown in FIG. 2B. The speed control process 82, initially controlled by a user input 90, begins by detecting an actuation level of the user input 90. The controller 70 receives a user input signal corresponding to the actuation level and subsequently, converts the user input signal detected at the user input 90 into a desired rotational speed of the surgical bur 18 corresponding to the actuation level. A first drive signal is supplied to the surgical instrument 10 to rotate the surgical bur 18 or other surgical tool at the desired speed and the speed control process ends.

The operation process 80 as described above compensates for unintended movement of the surgical bur 18 by adjusting the speed of the surgical bur 18. Adjusting the speed of the surgical bur 18 could consist of an increase in speed, a decrease in speed, a combination of both an increase and decrease (i.e. a pulsed rotational speed), or a comparable change in drive signal to end the chatter event. Unintended movement of the surgical bur 18 caused by chatter may lead to skiving, jumping, stalling, or any number of other undesirable motions by the handheld surgical instrument 10.

After the speed control process 82 is complete, and the system returns to the operation process 80, a continue operation step is included to illustrate that these processes 82, 84, 86 are occurring in a generally continuous manner while the handheld surgical instrument 10 is in use. Turning now to FIG. 2C, the current sensor process 84 is called after a time of continued operation. First, an instruction 84A of the current sensor is employed to determine the electrical current being drawn by the motor 12 of the surgical instrument 10 based on the drive signal. The electrical current may be determined by directly by way of a current sensing element, for example, a shunt resistor. Separate shunt resistors may be used to determine the electrical current in each phase of the motor 12. For example, in the case of a three phase motor, three shunt resistors may be used. Based on the electrical current determined, three current vectors may be calculated, which correspond to the drive signal and a time domain electrical current. Other current sensing elements are contemplated.

Subsequent to determining the electrical current in instruction 84A of the current sensor, a flux vector of the three-phase control signal may be calculated in instruction 84B. Here, the three current vectors, each corresponding to a phase current of one phase of the motor 12 are used as inputs for a Clark transformation. The Clark transformation converts the three current vectors into a flux vector comprising two orthogonal vectors, which produce the same net vector.

Similarly, the flux vector calculated from instruction 84B may be used as an input to instruction 84C, which performs a Park transformation. The Park transformation transforms the flux vector into a rotating reference frame to isolate the electrical current into a single quantity in the time domain. Here, the time electrical current is a scalar value that corresponds to the total electrical current drawn by the motor 12 during use.

Next, the controller 70 analyzes the sensed electrical current to identify if a chatter event may be occurring. In instruction 84D, the time domain electrical current is analyzed in a frequency domain electrical current to generate a harmonic signature. More specifically, a Fourier transform is performed on the time domain electrical current to generate a harmonic signature, which may be further analyzed to identify the chatter event. In some implementations, a fast Fourier transform may be performed on the time domain electrical current to generate the harmonic signature. The harmonic signature indicates one or more individual frequency components of the electrical current drawn by the motor 12. Said differently, the frequency of fluctuations in the electrical current is determined, and a magnitude of the fluctuation at each frequency is determined.

Once the harmonic signature of the electrical current has been generated, the harmonic signature may be used to identify the chatter event in instruction 84E. Here, the harmonic signature may be compared to a chatter signature that is indicative of a chatter event. In one instance the harmonic signature may be analyzed to determine is a resonant peak exists at a particular frequency (e.g., 10 kHz). The amplitude of the resonant peak may be compared to the amplitude of the non-resonant peaks and amplitudes above a peak threshold may be identified as a chatter event. Alternatively, based on the desired rotation speed of the bur, if the harmonic signature is an n-th order (e.g. $2^{nd}$ order, $3^{rd}$ order, $5^{th}$ order, etc) harmonic of the desired speed of the bur, a chatter event may be identified. For example, if a surgical bur 18 with ten flutes rotates at a desired speed of 60k RPM, a harmonic signature with a 100 Hz vibration may correspond to a chatter event.

Alternatively, the chatter signature may be defined by a resonant peak above a predetermined threshold. The harmonic signature is compared to the chatter signature and any amplitude peaks above the predetermined threshold may be identified as the chatter event. Here, the predetermined threshold may be stored in the memory. In some implementations, the chatter signature may be stored in the memory as a function of the resonant frequency and matched to the harmonic signature to identify the chatter event.

In other implementations, a plurality of chatter signatures may be stored in the memory, each chatter signature having characteristics corresponding to a parameter of the surgical bur 18 in use. In this instance, the controller 70 may be further instructed to select an appropriate chatter signature for comparison from the plurality of chatter signatures stored in the memory based on the bur parameter. The bur parameter may comprise one or more attributes of the surgical bur 18 such as bur geometry, bur type, bur material, quantity of flutes, and the like. The bur geometry may comprise size, such as length and diameter of the bur head, shank length, a measured natural frequency, a shape of the bur head, and other physical characteristics of the surgical bur 18.

It is contemplated that the controller 70 may look to a lookup table stored in the memory and check characteristics of the drive signal against entries in the lookup table. For example, if the handheld surgical instrument 10 is operating at 60k RPM with a current draw of 1 Ampere (A), these two values can be checked against the lookup table to confirm that 1A is an appropriate current draw for a speed of 60k RPM. A current fluctuation pattern could also be extrapolated from a series of current readings and that pattern checked against the lookup table. Chatter may result in identifiable changes to the current pattern that can be used to detect and identify chatter events.

The current sensor process may be tied to the specific construction of the surgical bur 18. Surgical burs may have a plurality of flutes that act as cutting surfaces and help remove cut tissue. Flute count may be related to which types of speed changes lead to a reduction in chatter as chatter frequency is often the frequency of the surgical bur 18 multiplied or divided by the number of flutes. If one of the harmonics of the sensed current pattern matches the flute count or a multiple of the flute count, this may be an indication that a chatter event is occurring.

The current sensor process 84 may also use machine learning to detect chatter events before they occur. Like chatter events can be inferred from fluctuations in the current drawn by the handheld surgical instrument 10, chatter events can also be anticipated in a similar manner. Machine learning may be used based on previously detected chatter events to continuously build a list of current fluctuation patterns which coincide with chatter events. For example, if a chatter event is determined through the process in FIG. 2C, the system could store the current pattern that existed shortly before the chatter event. The chatter algorithm process 86 may then be used to resolve the chatter event. Later, when the same pattern is detected during operation of the handheld surgical instrument 10, chatter may be preempted by the same change in rotational speed that previously resolved the chatter event. One such pattern could be the presence of a harmonic or harmonics in the drive signal as described above.

Once the current sensor process 84 has determined whether or not a chatter event exists the process is considered complete and the handheld surgical instrument 10 returns to the operation process 80. The decision step at the bottom of FIG. 2A depends on whether a chatter event was identified during the current sensor process 84. If no chatter event was identified, the handheld surgical instrument 10 continues to the speed control process 82. However, if a chatter event was identified, the chatter algorithm process 86 is called.

FIG. 2D shows the chatter algorithm process and the steps follow. First, a second drive signal is supplied to the motor 12 of the surgical instrument 10 based on the identified chatter event. Second, the current sensor process 84 is called to determine whether the chatter event still exists. Third, the process analyzes the electrical current to identify further chatter events, i.e., if the chatter event was resolved. If the chatter event was resolved and is no longer detected, the process returns to the operation process 80. If the chatter event is still identifiable, however, the chatter algorithm process 86 supplies a further drive signal and proceeds to the second step of the chatter algorithm process 86.

One exemplary rotational speed adjustment may be in the form of increasing, decreasing, or a combination of increasing and decreasing the rotational speed of the surgical bur 18. The chatter algorithm process 86 may increase the rotational speed until a chatter event is no longer detected or for a predetermined time period, and may do the same by decreasing the rotational speed. It is contemplated that a range of rotational speeds, 5k-100k RPM for instance, may be set so that the surgical bur 18 is not set to rotate at an ineffective or inappropriate speed. If the chatter algorithm process 86 were to bring the rotational speed to either an upper or lower limit, the rotational speed would be decreased or increased away from the limit until chatter is resolved.

Calculated adjustments may be made to the drive signal. One example based on the signal harmonics discussed above may be to adjust the drive signal such that the detected harmonic signature can no longer exist as a disruptive characteristic, such as chatter. Such an adjustment would require the controller 70, or another part of the console system 132, to perform calculations to calculate what manner of adjustment would be most likely to resolve the chatter event.

Figure 3:
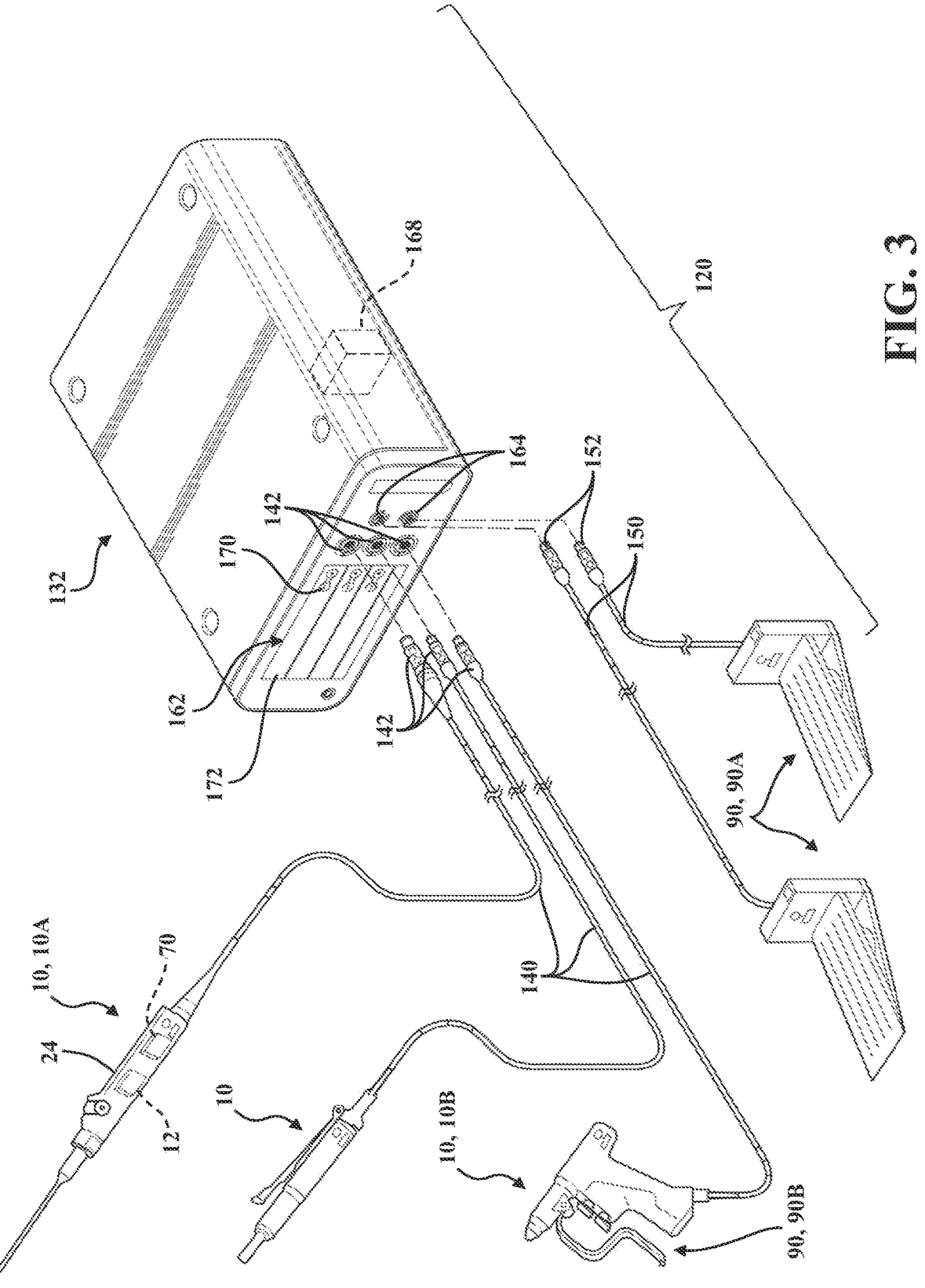
FIG. 3 is a partially exploded view of a console-based surgical bur system comprising a console system, a plurality of surgical instruments, and a plurality of input devices.

Referring to FIG. 3, a surgical bur system 120 is shown. The bur system 120 may comprise a handheld surgical instrument 10, illustrated here as a high-speed drill 10A, a user input 90, and a console system 132 for controlling the instrument 10 with an associated user input 90. The console system 132 receives a user input signal from the user input 90, illustrated here as a footswitch 90A, and supplies the first drive signal to control the associated instrument 10 during a surgical procedure. The console system 132 may further comprise one or more ports arranged on an exterior surface of a console body. The ports as shown here may comprise an instrument port 160 and a control port 164, which are configured to received corresponding plugs from the surgical instrument 10 and the user input 90, discussed below. In some implementations the instrument port 160 and the control port 164 may be interchangeable such that the surgical instrument 10 and the user input 90 may be plugged into either of the instrument port 160 and the control port 164, for example a USB port. In other implementations the instrument port 160 and the control port 164 may be unique, or different from each other, so as to prevent improper assembly.

In some implementations the bur system 120 may comprise a plurality of handheld surgical instruments 10 and a plurality of user inputs 90 in communication with the console system 132 for use during a surgical procedure. Similar to above, the console system 132 may comprise a plurality of instrument ports 160 and a plurality of control ports 164 configured to receive corresponding plugs from the plurality of surgical instruments 10 and the plurality of user inputs 90. Here, the console system 132 may further comprise a plurality of visual indicators arranged on the console body and configured for indicating which of the plurality of surgical instruments 10 and user inputs 90 correspond with one another. The bur system 120 is shown in FIG. 3 as, for exemplary purposes, controlling three handheld surgical instruments 10, but in other implementations, the system can control one, two, four, five, or any suitable number and type of instruments 10. Furthermore, the bur system 120 is shown as, for exemplary purposes, comprising two footswitches 90A, but in other implementations, the bur system 120 may comprise one, three, four, five, or any number of footswitches or other types of user input devices. The bur system 120 any number of visual indicators useful to indicate the association between the instrument ports and footswitch ports.

While the bur system 120 illustrated in FIG. 3 comprises two footswitches 90A as the user inputs 90, other user inputs 90 may be utilized. For example, a trigger switch 90B is shown coupled to an alternative surgical instrument 10B for actuation by the user to control the desired speed. Other user inputs 90 suitable for actuation by a surgeon or other personnel may similarly be utilized.

The user input 90 may comprise a connector line 150 configured to engage one of the control ports 164 for communication between the user input 90 and the console system 132. Each connector line 150 may terminate at one end that is coupled to a corresponding one of the user inputs 90 and terminate at an opposing end with a corresponding one of plugs 152 configured to engage the console system 132 as provided in the description below. In other implementations, the connector lines may terminate with a socket or any type of connector.

As mentioned above, the console system 132 may comprise a plurality of instrument ports 160 for communication with the surgical instrument 10. To this end, the surgical instrument 10 may comprise a connector line 140 terminated with a plug 142. The plug 142 is configured to engage one of the instrument ports 160 of the console system 132 to place the surgical instrument 10 in communication with the console system 132. Said differently, the plug 142 and the instrument port 160 cooperate to effect communication along the connector line 140 between the console system 132 and the surgical instrument 10.

While FIG. 3 illustrates that the console system 132 may comprise a display 162 positioned adjacent to the instrument ports 160, it is contemplated that the console system 132 can instead comprise one, two, four, or any number of instrument ports positioned on any suitable portion of the console body. The plugs 152 of the connector lines 150 associated with the user inputs 90 are capable of being connected to the plurality of control ports 164. The plurality of control ports 164 are spaced apart from the display 162, such that the plurality of instrument ports 160 are positioned between the control ports 164 and the display 162. However, other configurations of the instrument ports 160, the control ports 164, and the display 162 are contemplated.

The console system 132 further comprises a console controller 168 configured to associate one of the instrument ports 160 with one of the control ports 164 such that the user input 90 is operable to actuate a function of the handheld surgical instrument 10 connected to the associated instrument port 160. The console system 132 is may be coupled to a power source (not shown) to receive power therefrom and deliver the same to any one or more of the instruments 10 and the user inputs 90. More specifically, the console system 132 may provide electrical power to the surgical instrument to power the motor 12. The console system 132 may be further configured to provide data and control signals to the surgical instrument 10 via the connector line 150. For example, the console system 132 may supply DC power and a separate data signal to the surgical instrument 10. The data signal may facilitate communication between the console controller 168 and the controller 70 of the surgical instrument 10. The data signal may comprise, for example, a numerical value of a desired rotational speed, a PWM control signal, a parallel or serial bus, and the like, which instructs, or contains instructions to, the controller 70 to operate the motor 12. Alternatively, the console system 132 may provide a PWM power signal, which may be received at the controller 70, or may drive the motor 12 directly.

In order to facilitate detecting a chatter event and the chatter algorithm, the console controller 168 and the controller 70 of the surgical instrument 10 may each comprise a processor and a memory. The memory may be configured to store instructions for carrying out each of the steps of the operation process 80 described above. The processor may be capable of executing the instructions stored in the memory. In some implementations of the surgical bur system 120, the location of the console controller 168 and the controller 70 of the surgical instrument 10 may differ from the implementation illustrated herein. For example, the controller 70 may be housed in the console system 132 such that the memory and processor communicate with the surgical instrument 10 via the connector line 140. Alternatively, the console controller 168 and the controller 70 of the surgical instrument 10 may be combined into a single controller capable of performing the functions of each. In some implementations the memory may be located within the controller 70 and have parameters specific to the surgical instrument 10 in which it is located, while the processor is located in the console controller 168 and configured to perform the chatter event detection.

In a further implementation, the functions of the console controller 168 and the controller 70 of the surgical instrument 10 may be performed on a computer in communication with one or more of the console system 132 and the surgical instrument 10. This computer may be located locally, such as in the operating room, adjacent but outside of the operating room, or centrally located within a facility having several operating rooms and capable of servicing each operating room. Alternatively, the computer may be located remotely from the surgical instrument 10, such as in a centralized computing facility in communication with the operating room via the internet or other private communications network. Further, the processor and the memory may be located individually either locally or remotely. Said differently, the processor may be located in the controller 70 and arranged within the surgical instrument 10 and in communication with a memory located remotely and accessible via a cloud storage network. Similarly, the memory may be located within the controller 70 and have parameters specific to the surgical instrument 10 in which it is located, while the processor is located remotely and accessible via a cloud computing network to perform the chatter event detection.

In some implementations, the connector lines 140 for the handheld surgical instruments 10 and/or user inputs 90 may be omitted and the console may be connected wirelessly therewith. In this implementation the chatter event detection may be performed by the controller 70 in the handheld surgical instrument 10, or by the console system 132. In a further implementation the console system 132 may be fully integrated into the surgical instrument 10 and the chatter event detection performed entirely on the surgical instrument 10. Such an arrangement with the console system 132 integrated into the surgical instrument 10 may be preferred when using a battery powered surgical instrument (not shown).

The bur system 120 may further comprise a console input device 170 coupled to the console controller 168 and actuatable by a user to output one or more user output signals to cause the console controller 168 to associate one of the instrument ports 160 with one of the user inputs 90. In one implementation, the console input device 170 can be a touchscreen panel 172 or any other input device configured to permit a surgeon to indicate which user input assignments are wanted for the present operation. More specifically, the console controller 168 may comprise a circuit (not shown) that, based on instructions from the touchscreen panel 172 or other user input device, generates energization signals transmitted to the motors (not shown) or other power-consuming units (not shown) internal to the instruments 10 coupled to the associated instrument ports 160. The console controller 168 can be simultaneously connected to the plurality of handheld surgical instruments 10 through the corresponding plugs 142 and connector lines 140.

It is relevant to note that the order of operations described herein are not essential, exhaustive, or limiting. In other words, the execution of the operations may be performed in any order. Additional or fewer operations may exist other than those disclosed herein, and it is contemplated that executing a particular operation before another operation, during the execution of another operation, or after another operation is within the scope of this disclosure.

Further, in the disclosed implementations above, the chatter event is determined via the current aspect of the drive signal. However, it is also contemplated that other electrical aspects of the drive signal such as voltage or power could be used in place of current. Also, although the above implementations describe current sensing broadly as "measure current" or "sense current," this current sensing is not limited to the current value at a single moment in time. The current measurement could be a single value at a certain time, or it could be, among other methods, multiple measurements over a period of time along with a mathematical calculation of slope, gradient, difference, sum, product, or the application of the sensed current values to a specific mathematical formula.

Several instances have been discussed in the foregoing description. However, the aspects discussed herein are not intended to be exhaustive or limit the disclosure to any particular form. Various modifications to these aspects will be readily apparent to those skilled in the art, and the generic principles defined herein may be applied to other aspects without departing from the scope of the disclosure. The terminology that has been used is intended to be in the nature of words of description rather than of limitation. Many modifications and variations are possible in light of the above teachings and the disclosure may be practiced otherwise than as specifically described.

CLAUSES

I. A surgical bur system capable of rotating a surgical bur at a speed of at least 5,000 RPM comprising: a handheld surgical instrument comprising: a connector line having a proximal end and a distal end opposite the proximal end, a body coupled to the connector line, including a motor, a drive chuck coupled to the motor, a nose tube defining a lumen extending between proximal and distal ends, the nose tube being coupled to the body, a driveshaft at least partially disposed within the lumen of the nose tube and configured to rotate relative to the nose tube, and a surgical bur coupled to a distal region of the driveshaft; a console comprising: a controller, and a current sensor in electrical communication with the controller and the handheld surgical instrument for sensing an electrical current drawn by the motor, wherein the controller is configured to measure the electrical current drawn by the motor and identify a chatter event based on the measured electrical current; and a footswitch in communication with the console for controlling the speed of the surgical bur.

II. The surgical bur system of clause I, wherein the motor is configured to rotate the rotatable drive chuck at speeds of at least 50,000 RPM.

III. A console configured to provide a drive signal to a handheld surgical instrument comprising: at least one instrument port for being connected to a handheld surgical instrument, said handheld surgical instrument having a surgical bur, a footswitch port for being connected to a footswitch, and a controller configured to: determine a sensed electrical current drawn by the handheld surgical instrument, determine a chatter event based on the sensed electrical current, and adjust the speed of the surgical bur in response to the determined chatter event.

IV. A surgical console system configured to provide a drive signal to a surgical instrument comprising a rotatable bur, the surgical console system comprising: a processor and a memory, the memory storing instructions executable by the processor to: supply a first drive signal to the surgical instrument to rotate the bur at a desired speed; determine an electrical current drawn by the surgical instrument based on the drive signal; identify a chatter event based on the electrical current; and supply a second drive signal to the surgical instrument based on the identified chatter event.

V. The surgical console system of clause IV, wherein the second drive signal supplied to the surgical instrument rotates the bur at an alternate speed.

VI. The surgical console system of clause IV, further comprising an instrument port configured to engage with a corresponding connector of the surgical instrument for communication with the surgical instrument.

VII. The surgical console system of clause IV, further comprising a step of receiving a user input signal corresponding to the desired speed of the bur.

VIII. The surgical console system of clause VII, wherein the user controlled speed input is a footswitch.

IX. The surgical console system of clause IV, wherein the instruction to identify a chatter event is further defined as analyzing the electrical current in a frequency domain to generate a harmonic signature.

X. The surgical console system of clause IX, wherein the harmonic signature is generated by transforming the electrical current from a time domain to the frequency using a Fourier transform.

XI. The surgical console system of clause IX, wherein the instruction to identify the chatter event further comprises comparing the harmonic signature to a chatter signature stored in the memory.

XII. The surgical console system of clause XI, wherein the instruction to identify the chatter event further comprises selecting the chatter signature from a plurality of chatter signature based on a bur parameter.

XIII The surgical console system of clause XII, wherein the bur parameter is further defined as a bur geometry.

XIV. The surgical console system of clause XI, wherein the chatter signature stored in the memory is defined by a resonant peak.

XV. The surgical console system of clause X, wherein the instruction to identify the chatter event further comprises determining whether the harmonic signature is an n-th order harmonic of the desired speed of the bur.

XVI. The surgical console system of clause X, wherein the instruction to determine the electrical current comprises calculating a flux vector of the surgical instrument.

XVII. The surgical console system of clause XVI, wherein the instruction to calculate the flux vector comprises calculating a transformation of measured phase currents of the surgical instrument.

XVIII. A surgical bur system capable of rotating a surgical bur at a speed of at least 5,000 RPM, the surgical bur system comprising: a handheld surgical instrument comprising: a body; a motor disposed in the body; a surgical bur coupled to the motor and configured to rotate relative to the body; a console in communication with the handheld surgical instrument and configured to provide a drive signal to the motor, the console comprising: a processor and a memory, the memory storing instructions executable by the processor to: supply a first drive signal to the handheld surgical instrument to rotate the surgical bur at a desired speed; determine a electrical current drawn by the handheld surgical instrument based on the drive signal; identify a chatter event based on the electrical current; and supply a second drive signal to the handheld surgical instrument based on the identified chatter event.

XIX. The surgical console system of clause XVIII, wherein the second drive signal supplied to the handheld surgical instrument rotates the bur at an alternate speed.

XX. The surgical bur system of clause XVIII, further comprising a user input in communication with the console configured to adjust the desired speed of the surgical bur.

XXI. The surgical bur system of clause XVIII, wherein the instruction to identify a chatter event is further defined as analyzing the electrical current in a frequency domain to generate a harmonic signature.

XXII. The surgical bur system of clause XXI, wherein the harmonic signature is generated by transforming the electrical current from a time domain to the frequency using a Fourier transform.

XXIII The surgical bur system of clause XXII, wherein the instruction to determine the electrical current comprises calculating a flux vector of the surgical instrument.

XXIV. The surgical bur system of clause XXIII, wherein the instruction to calculate the flux vector comprises calculating a transformation of measured phase currents of the surgical instrument.

XXV. The surgical bur system of clause XXI, wherein adjusting the drive signal supplied to the handheld surgical instrument comprises calculating chatter frequency.

XXVI. The surgical bur system of clause XXV, wherein adjusting the drive signal supplied to the handheld surgical instrument further comprises calculating a rotation speed that based on the chatter frequency that will not result in a chatter event.

XXVII. A surgical console system configured to provide a drive signal to a surgical cutting tool, the surgical console system comprising: a processor and a memory, the memory storing instructions executable by the processor to: supply a first drive signal to the surgical instrument to rotate the surgical cutting tool at a desired speed; determine an electrical current drawn by the surgical instrument based on the drive signal; identify a chatter event based on the electrical current; and supply a second drive signal to the surgical instrument based on an identified chatter event.

XXVIII. A method of operating a surgical instrument having a rotatable bur, the method comprising steps of: supplying a first drive signal to the surgical instrument to rotate the bur at a desired speed; determining an electrical current drawn by the surgical instrument based on the drive signal; identifying a chatter event based on the electrical current; and supplying a second drive signal to the surgical instrument based on the identified chatter event.

XXIX. The method of clause XXVIII, wherein the step of identifying a chatter event is further defined as analyzing the electrical current in a frequency domain to generate a harmonic signature.

XXX. A computer-readable medium comprising a computer program, the computer program comprising instructions which, when the program is executed by a processor, cause the processor to: supply a first drive signal to the surgical instrument to rotate the bur at a desired speed; determine an electrical current drawn by the surgical instrument based on the drive signal; identify a chatter event based on the electrical current; and supply a second drive signal to the surgical instrument based on the identified chatter event.

What is claimed is:

1. A surgical console system configured to provide a drive signal to a surgical instrument comprising a rotatable bur configured to contact a tissue surface, the surgical console system comprising:

a processor and a memory, the memory storing instructions executable by the processor to:

supply a first drive signal to the surgical instrument to rotate the bur at a rotational speed;

determine an electrical current drawn by the surgical instrument based on the drive signal;

identify a chatter event based on the electrical current, wherein the chatter event is characterized by undesirable vibration of the bur during contact between the tissue surface and the bur; and supply a second drive signal to the surgical instrument based on an identified chatter event.

2. The surgical console system of claim 1, wherein the second drive signal supplied to the surgical instrument rotates the bur at an alternate speed.

3. The surgical console system of claim 1, further comprising an instrument port configured to engage with a corresponding connector of the surgical instrument for communication with the surgical instrument.

4. The surgical console system of claim 1, further comprising a step of receiving a user input signal corresponding to the rotational speed of the bur.

5. The surgical console system of claim 1, wherein the instruction to identify a chatter event is further defined as analyzing the electrical current in a frequency domain to generate a harmonic signature.

6. The surgical console system of claim 4, wherein the user input signal is received from a footswitch.

7. The surgical console system of claim 5, wherein the harmonic signature is generated by transforming the electrical current from a time domain to the frequency domain using a Fourier transform.

8. The surgical console system of claim 5, wherein the instruction to identify the chatter event further comprises comparing the harmonic signature to a chatter signature stored in the memory.

9. The surgical console system of claim 7, wherein the instruction to identify the chatter event further comprises determining whether the harmonic signature is an n-th order harmonic of the rotational speed of the bur.

10. The surgical console system of claim 7, wherein the instruction to determine the electrical current comprises calculating a flux vector of the surgical instrument.

11. The surgical console system of claim 8, wherein the instruction to identify the chatter event further comprises selecting the chatter signature from a plurality of chatter signature based on a bur parameter.

12. The surgical console system of claim 8, wherein the chatter signature stored in the memory is defined by a resonant peak.

13. The surgical console system of claim 11, wherein the bur parameter is further defined as a bur geometry.

14. A surgical bur system capable of rotating a surgical bur at a speed of at least 5,000 RPM, the surgical bur system comprising:

a handheld surgical instrument comprising:

a body;

a motor disposed in the body;

a surgical bur coupled to the motor and configured to rotate relative to the body and contact a tissue surface;

a console in communication with the handheld surgical instrument and configured to provide a drive signal to the motor, the console comprising:

a processor and a memory, the memory storing instructions executable by the processor to:

supply a first drive signal to the handheld surgical instrument to rotate the surgical bur at a rotational speed;

determine an electrical current drawn by the handheld surgical instrument based on the drive signal;

identify a chatter event based on the electrical current, wherein the chatter event is characterized by undesirable vibration of the bur during contact between the tissue surface and the bur; and supply a second drive signal to the handheld surgical instrument based on an identified chatter event.

15. The surgical bur system of claim 14, wherein the second drive signal supplied to the handheld surgical instrument rotates the surgical bur at an alternate speed.

16. The surgical bur system of claim 14, further comprising a user input in communication with the console configured to adjust the rotational speed of the surgical bur.

17. The surgical bur system of claim 14, wherein the instruction to identify a chatter event is further defined as analyzing the electrical current in a frequency domain to generate a harmonic signature.

18. The surgical bur system of claim 17, wherein the harmonic signature is generated by transforming the electrical current from a time domain to the frequency domain using a Fourier transform.

19. The surgical bur system of claim 17, wherein adjusting the drive signal supplied to the handheld surgical instrument comprises calculating chatter frequency.

20. The surgical bur system of claim 19, wherein adjusting the drive signal supplied to the handheld surgical instrument further comprises calculating a rotation speed that based on the chatter frequency that will not result in a chatter event.

\* \* \* \* \*